US00PP16176P3

(12) United States Plant Patent
Cosner et al.

(10) Patent No.: US PP16,176 P3
(45) Date of Patent: Jan. 3, 2006

(54) ***IMPATIENS* PLANT NAMED 'TIWHIT'**

(50) Latin Name: *Impatiens walleriana*
Varietal Denomination: TiWhit

(76) Inventors: Harlan B. Cosner, 14389 E. Evans Creek Rd., Rogue River, OR (US) 97537; Susan Cosner, 14389 E. Evans Creek Rd., Rogue River, OR (US) 97537

( * ) Notice: Subject to any disclaimer, the term of this patent is extended or adjusted under 35 U.S.C. 154(b) by 564 days.

(21) Appl. No.: 10/401,993

(22) Filed: Mar. 27, 2003

(65) Prior Publication Data

US 2004/0194184 P1 Sep. 30, 2004

(51) Int. Cl.
*A01H 5/00* (2006.01)

(52) U.S. Cl. ..... Plt./317

(58) Field of Classification Search ..... Plt./317
See application file for complete search history.

*Primary Examiner*—Anne Marie Grunberg
*Assistant Examiner*—Annette H Para
(74) *Attorney, Agent, or Firm*—Ganz Law, PC; Bradley M. Ganz

(57) ABSTRACT

A new and distinct double-flowered *Impatiens walleriana* named 'TiWhit', producing white flowers that often show a light pink blush in temperatures warmer than 70° F. minimums; dark green foliage; medium vigor; fully double flowers held above or beyond the foliage on strong peduncles and pedicels; with a mounded growth habit.

1 Drawing Sheet

Latin name of the genus and species and variety denomination: *Impatiens walleriana* plant and known by the cultivar name 'TiWhit'.

BACKGROUND—FIELD OF INVENTION

The present invention relates to a new and distinct cultivar botanically known as '*Impatiens walleriana*' and by the cultivar name 'TiWhit', which is shown in the photograph accompany this specification.

The cultivar was developed and selected in a controlled breeding program in a controlled environment in Broadbent, Oreg. by the inventors, Harlan Cosner and Sue Cosner, as described herein. The plants may be used in landscaping, window, and hanging baskets and flower gardens. The plants are generally classed as an annual bedding plant.

The accompanying photograph illustrates the overall appearance of the new *Impatiens*. The photo shows the color as true as reasonably possible to obtain in color reproductions of this type. Color in the photograph may differ slightly from the color values cited in the detailed botanical description which accurately described the color of the new *Impatiens*.

BACKGROUND—DESCRIPTION OF THE PRIOR ART

The only known cultivar of relevant prior art is believed to be an '*Impatiens walleriana*' named 'Tioga White,' subject of U.S. Plant Pat. No. 10,345.

COMPARISON

The *impatiens* plant of the present invention differs from prior plants, namely 'Tioga White' in at least the following ways:

1. The flower color of 'Tioga White' is white and remains white in warm weather. The flower color of TiWhit is white but often takes on a pink tinge in warm weather.
2. The plant of 'TiWhit' is much larger than plant of Tioga White.
3. The plant of 'TiWhit' is a double-flowered *impatiens* differing from its pollen parent in both flower color and fertility.
4. 'TiWhit' is a double-flowered *impatiens* with reproductive organs replaced by sterile petaloids.

These and other distinguishing characteristics will be apparent to persons skilled in the art.

BACKGROUND—DISCOVERY AND PARENTAGE

The present cultivar was developed by standard cross-pollination. The pollen producing parent was an unpatented double '*Impatiens walleriana*' designated M-BR-39, and the seed producing parent was an unpatented semi-double-flowered *impatiens* designated BR-D-1003. The seed parent's flower color was white, and the pollen parent's flower color was a blush white.

The cross was made in the breeders' controlled breeding program at Broadbent, Oreg. The first asexual reproduction was also made at Broadbent, Oreg. Successive asexual generations produced from cuttings with two or more leaves have shown the cultivar to be stable.

The cultivar is unique either in one or a combination of the characteristics described herein. It is a new, complete double-flowered '*Impatiens walleriana*' producing white flowers that often show a light pink blush in temperatures warmer than 70° F. minimums; dark green foliage; medium vigor; fully double flowers held above or beyond the foliage on strong peduncles and pedicels; and a mounded growth habit.

Color references are according to The Royal Horticultural Society Colour Chart, except where general terms of ordinary dictionary significance are used.

DETAILED DESCRIPTION

The following description relates to the following environmental and cultural practices at Rogue River, Oreg., on or about Mar. 1, 2003.

The photograph illustrates the overall appearance of the cultivar described herein.

The photograph was taken of a TiWhit plant of about 10 weeks of age from rooted cuttings, at first inflorescence. There may be variations between the colors in the photograph and the colors in the following description due to light reflectance, or the amount of blue or red light captured in the film. If such variations occur, the written description shall control.

The plant of the present invention has not been observed in all possible environmental and/or cultural conditions. The phenotype may vary significantly with variations in environment such as temperature, light level, humidity and also with cultural practices such as fertility, soil, and water quality.

Container—6-inch Azalea containers.

Medium—Peat-lite type of soil less medium.

Greenhouse covering—Double layer Polyethylene with 50% shade applied above the covering.

Minimum temperature—70° F.

Maximum temperature—75° F.

Light levels—1000 to 2000 ft candles.

Fertilizer—20-10-20 with trace elements applied twice followed by one leaching with clear water.

Cutting type—Lateral stems with two or more leaves.

Propagation:

*Type of cutting.*—Lateral stems with two or more leaves were used for asexual reproduction.

*Time to initiate roots.*—Generally about 7 to 10 days at soil temperature of 72° F.

Appearance and form of mature plant:

*Plant form and habit.*—Mounded and of medium vigor.

*Plant size.*—Plants mature at about 16 cm. in height and about 30 cm. in width. Both of these measurements are a function of age, environmental and cultural practices, and can vary accordingly.

*Rooting description.*—The roots are fibrous and well-branched.

*Rooting ability.*—Easy, no hormones needed.

*Branching habit.*—Plants are self-branching. Stems are strong and freely produced. The number of stems depends upon cultural practices, age of stems used as cuttings and the number of growth buds present on the cutting when stuck.

*Stems.*—Stems are freely produced and no pinching to induce branching is needed. Color is close to 144A. The stems at maturity are generally at least 3 mm in diameter at the internodes, and the internode length is generally at least 0.5 cm in length.

*Foliage shape and size.*—Shape is ovate with cuneate to attenuate base; crenate margin, margin having tiny spines of an undeterminable greenish color, each being a less than 1 mm in length, and protruding perpendicularly outwards from the leaf edge in direction and parallel with the leaf surfaces from between the lobes of the crenate margin; and an acuminate apex. Size of largest is about 3 cm long; about 3 cm wide.

*Foliage color.*—Adaxial surface close to137A; abaxial surface close to 147B; abaxial surface venation is close to 147B; adaxial surface venation, main vein at base is closest to 144A, lateral veins are barely distinguishable but appear closest to 137B.

*Foliage texture.*—Smooth and flat.

*Petioles.*—Petioles are about 2 cm long, half round, flat on upper surface which is about 2.5 mm wide, depth of about 1 mm. Adaxial surface color appears to be between 146C and 146D but does easily not match any color in the chart; abaxial surface color appears to be close to 146C to 146D.

*Natural flowering season.*—Year around in greenhouse conditions, and the frost-free period from spring through fall when planted outdoors. Flowers are produced continuously throughout the flowering season.

*Bud size, shape & color.*—The buds prior to opening are about 1 cm in length; about 0.75 cm in diameter; shape is ovate. Bud color prior to opening is close to 142 B on top and close to 142C on bottom.

*Time to flower.*—Flowering begins at about 10 weeks form rooted cuttings.

*Duration of flower.*—Each flower generally lasts about 5 days at 75° F. maximum and 70° F. minimum temperature.

*Flowers borne.*—Above or beyond the foliage.

*Flower count.*—Usually two or more open flowers per stem.

*Flower texture.*—Smooth and satiny.

*Flower fragrance.*—None detected.

*Flower color.*—Petals/petaloids — Adaxial surface is lighter than 155D but may show a pinkish overtone in high temperatures. Abaxial surface is lighter than 155D.

*Flower size and shape.*—Generally, at least 3.5 cm wide; generally at least 1 cm deep. The above measurements refer to the larger flowers, and the flower size was taken during winter low light when the flowers are the smallest. During spring and summer, the flowers are generally much larger than the above measurements and as much as double the described size.

*Petal size and shape.*—The largest petals are generally at least 1 cm. wide and at least 1.5 cm. deep; obovate to exaggerated obovate in shape with obtuse to retuse apex, entire margin, and cuneate to obtuse base.

*Petal count.*—Generally about 25 or more.

*Calyx.*—Calyx consists of generally one sepal and one spur. The spur is generally about 2 cm long, and about 2 mm in diameter at sepal end; shape is an acicular tapering tube about 1 mm in diameter at the sepal end, and it is attached toward the base of the sepal in a peltate manner. Color is close to 145A in color. The sepal generally measures about 0.75 cm wide, and about 1.25 cm long; ovate in shape with anacute apex, entire margin, and obtuse to cordate base; adaxial surface is lighter than 149D with a green spot close to 142B where the spur connects; the abaxial surface is lighter than 149D.

*Peduncles.*—Generally at least 1.75 cm long; about 2 mm in diameter; colored close to 144A. Good strength.

*Pedicels.*—Generally two or more per peduncle. Each is generally at least 1.75 cm in length, and at least 1 mm in diameter. Color is close to 144B but tends to be between 144A and 144B. Good strength.

*Reproductive organs.*—The reproductive organs are replaced with sterile petaloids.

*Disease resistance.*—Disease resistance has not been tested.

*Dampness resistance.*—The plant has shown a good ability to hold the flowers in an outward manner during summer rains.

*Cold/heat resistance.*—Plant flowers well in summer heat.

CHART 1—COLOR CODE

*Stems.*—144A.
*Foliage abaxial surface.*—147B.
*Foliage abaxial surface venation.*—147B.
*Foliage adaxial surface.*—137A.
*Foliage adaxial surface venation.*—144A, 137B.
*Petiole abaxial surface.*—146C, 146D.
*Petiole adaxial surface.*—146C, 146D.
*Petals/petaloids abaxial surface.*—155D.
*Petals/petaloids adaxial surface.*—155D.
*Bud top.*—142B.
*Bud bottom.*—142C.
*Peduncles.*—144A.
*Pedicels.*—144A, 144B.
*Sepals abaxial.*—149D.
*Sepals adaxial.*—149D, 142B.
*Spur.*—145A.

What is claimed:

1. A new and distinct cultivar of double-flowered *Impatiens walleriana* plant named 'TiWhit', as illustrated and described herein.

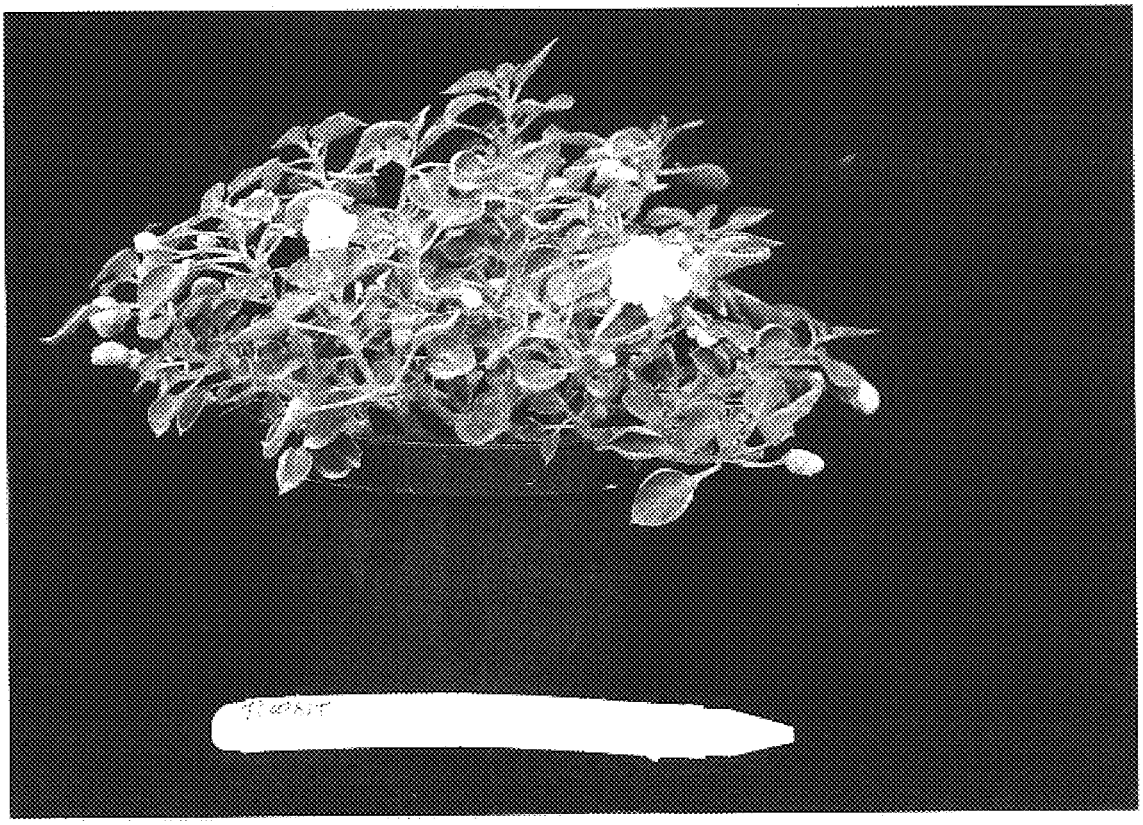

* * * * *